United States Patent [19]

Curran et al.

[11] 4,010,179

[45] Mar. 1, 1977

[54] 1-(PARA-SUBSTITUTED-PHENYL)-1H-TETRAZOLES

[75] Inventors: William Vincent Curran, Pearl River, N.Y.; Andrew Stephen Tomcufcik, Old Tappan, N.J.; Adma Schneller Ross, Suffern, N.Y.

[73] Assignee: American Cyanamid Company, Stamford, Conn.

[22] Filed: Nov. 10, 1975

[21] Appl. No.: 630,563

Related U.S. Application Data

[63] Continuation-in-part of Ser. No. 470,083, May 15, 1974, abandoned.

[52] U.S. Cl. ............................ 260/308 D; 424/269
[51] Int. Cl.² ....................................... C07D 257/04
[58] Field of Search .............................. 260/308 D

[56] References Cited

UNITED STATES PATENTS

| | | | |
|---|---|---|---|
| 3,767,667 | 10/1973 | Kamiya et al. | 260/308 |
| 3,830,928 | 8/1974 | Mrozik | 260/308 |

OTHER PUBLICATIONS

*Chem. Abstr.*, vol. 43, 1864–1865, (1949).

*Primary Examiner*—Frederick E. Waddell
*Attorney, Agent, or Firm*—Edward A. Conroy, Jr.

[57] ABSTRACT

This disclosure describes compounds of the class of 1-(para-substituted-phenyl)-1H-tetrazoles which possess anti-microbial and anti-neoplastic activity.

7 Claims, No Drawings

1-(PARA-SUBSTITUTED-PHENYL)-1H-TETRAZOLES

CROSS REFERENCE TO RELATED APPLICATION

This application is a continuation-in-part of our copending application Ser. No. 470,083, filed May 15, 1974, now abandoned.

BRIEF SUMMARY OF THE INVENTION

This invention relates to new organic compounds and, more particularly, is concerned with novel 1-phenyl-1H-tetra-zoles substituted in the para-position of the phenyl moiety with various sulfur and fluorine containing functional groups. The novel compounds of the present invention may be represented by the following general formula:

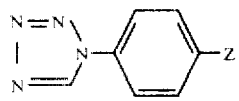

wherein Z is fluoromethylthio, fluoromethylsulfinyl, fluoromethylsulfonyl, difluoromethylthio, difluoromethylsulfinyl or difluoromethylsulfonyl. This invention is also concerned with novel methods of preparing these compounds.

DETAILED DESCRIPTION OF THE INVENTION

The novel compounds of the present invention are obtainable as white to pale yellow crystalline materials having characteristic melting points and absorption spectra and which may be purified by recrystallization from common organic solvents such as methanol, ethanol, dimethylformamide, acetone, chloroform, ethyl acetate and the like. They are appreciably soluble in non-polar organic solvents such as diethyl ether, benzene, toluene, and the like but are relatively insoluble in water.

The novel compounds of the present invention are useful as antimicrobial agents and possess broad spectrum activity in vivo against Gram-negative and Gram-positive bacteria. These new antimicrobial agents are thereby potentially useful as therapeutic agents in treating bacterial infections in mammals. They are also useful as additives to materials which are subject to microbial deterioration such as cutting oils and fuel oils. They may also be incorporated in soaps, shampoos, and topical compositions for the treatment of wounds and burns. The usefulness of these new antimicrobial agents was demonstrated by their ability to control systemic lethal infections in mice in the following test procedure.

The animals used were Carworth Farms CF-1 strain female mice approximately 6 weeks old and averaging 18–22 grams in weight. Infections were produced by intraperitoneal injections of a 0.5 ml. volume (a lethal dose) of a trypticase soy broth (TSP) dilution (as indicated in Table I) of a 5 hour TSP blood culture of the microorganisms listed in Table I below.

TABLE I

| Microorganisms | TSP dilution of a 5 hour TSP culture |
| --- | --- |
| Proteus mirabilis ATCC 4671 | 1:40 |

TABLE I-continued

| Microorganisms | TSP dilution of a 5 hour TSP culture |
| --- | --- |
| Escherichia coli 311 | $10^{-3}$ |

The test compounds were administered in a single 0.5 ml. oral tubing dose in 0.2% aqueous agar immediately after infection at the indicated levels. The results are set forth in Table II below as percent effectiveness (alive/total) at 2 days post infection for each dosage level.

TABLE II

| Dosage Level (mg./kg. of body weight) | Alive/Total with Escherichia coli | |
| --- | --- | --- |
|  | (A) | (B) |
| 128 | 4/5 | 5/5 |
| 64 | 3/5 | 3/5 |
| 32 | 2/5 | 1/5 |
| 16 | 1/5 | 2/5 |
| 8 | 1/5 | 0/5 |
| Infected Non-treated Controls | 5/20 | |

| | Alive/Total with Proteus mirabilis | |
| --- | --- | --- |
|  | (A) | (B) |
| 128 | 5/5 | 4/5 |
| 64 | 5/5 | 2/5 |
| 32 | 3/5 | 2/5 |
| 16 | 1/5 | 0/5 |
| 8 | 1/5 | 0/5 |
| Infected Non-treated Controls | 2/20 | |

(A) 1-[p-(difluoromethylthio)phenyl]-1H-tetrazole
(B) 1-[p-(difluoromethylsulfonyl)phenyl]-1H-tetrazole The novel compounds of the present invention possess antineoplastic activity which was demonstrated by the following test procedure.

Tests for antitumor activity were conducted in male or female $BDF_1$ ($C_{57}BL/_6 \times DBA/_2$) or $CDF_1$ ($Balb/_c \times DBA/_2$) mice weighing 16–20 grams. Mice were inoculated intraperitoneally (IP) with $10^5/0.25$ ml. cells of lymphoid leukemia L1210. The tumor line is maintained by weekly IP passages in $DBA/_2$ mice. The compounds evaluated were 1-(p-fluoromethylsulfonylphenyl)tetrazole; 1-[p-(difluoromethylsulfonyl)phenyl]-1H-tetrazole and 1-[p-(difluoromethylthio)phenyl]-1H-tetrazole. The vehicle employed for the administration of the compounds was 0.2% agar (Difco) in physiological saline. The compounds were administered IP or by gavage in a volume of 0.5 ml. per mouse. The various treatment regimens utilized with the compounds are noted in the tables.

The activity of the compounds was evaluated by comparing the mean survival time (MST) of the treated mice to the MST of non-treated controls. A compound was considered active if an increase in MST of ≥ 25% was achieved among the treated animals*.

*Cancer Chemotherapy Reports, Part 3, Volume 3, No. 2, September 1972. "Protocols for Screening Chemical Agents and Natural Products Against Animal Tumors and Other Biological Systems."

TABLE III

Effect of 1-(p-fluoromethylsulfonylphenyl)tetrazole Against the L1210 Tumor in Mice[1]
(Intraperitoneal Treatment)

| Compound | Dose[2] | Average Day of Death[3] | % Increase in Survival Time[4] |
| --- | --- | --- | --- |
| 1-(p-fluoromethyl-sulfonylphenyl)tetrazole | 100 | 11.2 | 42 |
|  | 50 | 14.4 | 82 |

TABLE III-continued
Effect of 1-(p-fluoromethylsulfonylphenyl)tetrazole Against the L1210 Tumor in Mice[1]
(Intraperitoneal Treatment)

| Compound | Dose[2] | Average Day of Death[3] | % Increase in Survival Time[4] |
|---|---|---|---|
| Methotrexate | 25 | 11.5 | 46 |
|  | 1.8 | 14.6 | 85 |
| Control[5] | — | 7.9 | — |

[1]CD$_2$F$_1$, female mice inoculated IP with 10⁵ L1210 cells per mouse, 10 mice per group.
[2]1-(p-fluoromethylsulfonylphenyl)tetrazole inoculated IP, daily, from the 1st through the 9th day after inoculation of tumor cells. Methotrexate inoculated IP, daily, from day 4 until day of death.
[3]100% mortality among treated and control mice.
[4]National Cancer Institute screening protocols require a minimal 25% increase in survival time for a compound to be considered for further evaluation.
[5]Placebo-treated (0.2% Noble agar in saline) from day 1 through day 9 after inoculation of tumor cells.

TABLE IV
Effect of Treatment Schedule on the Activity of 1-(p-fluoromethylsulfonylphenyl)tetrazole Against L1210 in Mice[1]
(Intraperitoneal Treatment)

| Compound | Dose | Day of Treatment following Inoculation of Tumor[2] | Average Day of Death[3] | % Increase in Survival Time[4] |
|---|---|---|---|---|
| 1-(p-fluoromethylsul-fonylphenyl)tetrazole | 200 | 1 | 9.8 | 15 |
|  | 100 | 1 | 9.2 | 8 |
|  | 50 | 1 | 8.9 | 4 |
| 1-(p-fluoromethylsul-fonylphenyl)tetrazole | 200 | 2,6 | 12.5 | 47 |
|  | 100 | 2,6 | 10.3 | 21 |
|  | 50 | 2,6 | 9.1 | 7 |
| 1-(p-fluoromethylsul-fonylphenyl)tetrazole | 100 | 1,5,9 | 11.8 | 39 |
|  | 50 | 1,5,9 | 9.5 | 12 |
| Methotrexate | 1.8 | 4——→Death | 15.2 | 79 |
| Control[5] |  |  | 8.5 |  |

[1]CD$_2$F$_1$ female mice inoculated with 10⁵ L1210 cells per mouse; 10 mice per group.
[2]1-(p-fluoromethylsulfonylphenyl)tetrazole and methotrexate inoculated IP on the indicated days following inoculation of L1210 cells.
[3]100% mortality among treated and control mice.
[4]National Cancer Institute screening protocols require a minimal 25% increase in survival time for a compound to be considered for further evaluation.
[5]Placebo-treated on day 1, 5 and 9 following inoculation of L1210 cells.

TABLE V
Effect of Treatment Schedule on the Activity of 1-(p-fluoromethylsulfonylphenyl)tetrazole Against L1210 in Mice[1]
(Oral Treatment)

| Compound | Dose (mg./kg.) | Day of Treatment Following Inoculation of Tumor[2] | Average Day of Death[3] | % Increase in Survival Time[4] |
|---|---|---|---|---|
| 1-(p-fluoromethyl-sulfonylphenyl)-tetrazole | 800 | 1 | 11.9 | 29 |
|  | 400 | 1 | 12.0 | 30 |
| 1-(p-fluoromethyl-sulfonylphenyl)-tetrazole | 400 | 2,6 | 11.1 | 21 |
|  | 200 | 2,6 | 13.5 | 47 |
|  | 100 | 2,6 | 11.5 | 25 |
| 1-(p-fluoromethyl-sulfonylphenyl)-tetrazole | 400 | 1,5,9 | 10.4 | 13 |
|  | 200 | 1,5,9 | 12.1 | 32 |
|  | 100 | 1,5,9 | 11.3 | 23 |
| Methotrexate | 1.8 | 4——→Death | 17.1 | 86 |
| Control[5] |  |  | 9.2 |  |

[1]BDF$_1$ female mice inoculated with 10⁵ L1210 cells per mouse; 10 mice per group.
[2]1-(p-fluoromethylsulfonylphenyl)tetrazole administered by gavage and methotrexate IP on the indicated days following inoculation of L1210 cells.
[3]100% mortality among treated and control mice.
[4]National Cancer Institute screening protocols require a minimal 25% increase in survival time for a compound to be considered for further evaluation.
[5]Placebo-treated on day 1, 5 and 9 following inoculation of L1210 cells.

TABLE VI

Effect of 1-(p-fluoromethylsulfonylphenyl)tetrazole Against
the L1210 Tumor in Mice[1]
(Oral Treatment)

| Compound | Dose (mg./kg.)[2] | Average Day of Death[3] | % Increase in Survival Time[4] |
|---|---|---|---|
| 1-(p-fluoromethylsul- fonylphenyl)tetrazole | 200 | 12.2 | 27 |
|  | 100 | >14.8 | >54 |
|  | 50 | 13.4 | 34 |
| Cytoxan | 50 | 14.2 | 42 |
|  | 25 | 11.8 | 18 |
| 5-Fluorouracil | 20 | 14.6 | 52 |
| Control[5] |  | 9.6 |  |

[1]$CD_2F_1$ female mice inoculated IP with $10^5$ L1210 cells per mouse; 5 mice per group.
[2]1-(p-fluoromethylsulfonylphenyl)tetrazole administered by gavage, daily, from the 1st through the 9th day after inoculation of tumor cells. 5-fluorouracil inoculated IP, daily, from day 1 until day 9.
[3]100% mortality among treated and control mice with the exception of a single survivor (1/5) in the group treated orally with 100 mg./kg./day of 1-(p-fluoromethylsulfonylphenyl)tetrazole.
[4]National Cancer Institute screening protocols require a minimal 25% increase in survival time for a compound to be considered for further evaluation.
[5]Placebo-treated (0.2% Noble agar in saline) from day 1 through day 9 after inoculation of tumor cells.

TABLE VII

Effect of Treatment Schedule on the Activity of 1-[p-(difluoromethyl-
sulfonyl)-phenyl]-1H-tetrazole Against L1210 in Mice[1]
(Intraperitoneal Treatment)

| Compound | Dose (mg./kg.) | Day of Treatment Following Inoculation of Tumor[2] | Mean Survival Time | % Increase in Survival Time[3] |
|---|---|---|---|---|
| 1-[p-(difluoromethyl- sulfonyl)-phenyl]-1H- tetrazole | 200 | 2,6 | 11.6 | 36 |
|  | 100 | 2,6 | 12.2 | 43 |
|  | 50 | 2,6 | 15.7 | 81 |
|  | 25 | 2,6 | 10.6 | 25 |
| 5-Fluorouracil | 60 | 2,6 | >17.8 | >109 |
|  | 200 | 1,3,9 | 9.8 | 13 |
|  | 100 | 1,3,9 | 11.6 | 33 |
|  | 50 | 1,3,9 | 13.4 | 54 |
|  | 25 | 1,3,9 | 10.6 | 22 |
| 5-Flourouracil | 60 | 1,3,9 | >17.0 | >100 |
|  | 100 | 1→9 | 7.4 | 0 |
|  | 50 | 1→9 | 10.8 | 27 |
|  | 25 | 1→9 | 12.4 | 46 |
| 5-Flourouracil | 20 | 1→9 | >18.0 | >112 |
| Control |  |  | 8.5 |  |

[1]BDF, Female mice inoculated with $10^5$ L1210 cells per mouse; 5 mice per group.
[2]Drugs administered IP in volume of 0.5 ml. on indicated days following inoculation of L1210 cells.
[3]National Cancer Institute screening protocols require a minimal 25% increase in survival time for a compound to be considered for further evaluation.

TABLE VIII

Activity of 1-[p-(difluoromethylthio)phenyl]-1H-tetrazole
Against L1210 in Mice[1]

| Compound | Dose (mg./kg.) | Treatment Schedule-Days[2] | Mean Survival Time-Days | % Increase In MST |
|---|---|---|---|---|
| 1-[p-(difluoro- methylthio)- phenyl]-1H-tetra- zole | 100 | 1 thru 9 | 8.4 | <1 |
|  | 50 | 1 thru 9 | 13.8 | 44 |
|  | 25 | 1 thru 9 | 12.8 | 33 |
| 5-Fluorouracil | 20 |  | 14.4 | 50 |
| Control | — |  | 9.6 |  |

[1]$CDF_1$ female mice inoculated with $10^5$ L1210 cells per mouse; 5 mice per group.
[2]Drugs administered IP in a volume of 0.5 ml. on days 1 through 9 following inoculation of L1210 cells.

The invention will be described in greater detail in conjunction with the following specific examples.

EXAMPLE 1

Preparation of
1-[p-(difluoromethylthio)phenyl]-1H-tetrazole

A mixture of p-(difluoromethylthio)aniline (4.0 g.), sodium azide (4.0 g.), triethyl orthoformate (25 ml.), and acetic acid (25 ml.) was heated at 95° C. for 4.5 hours and then evaporated at reduced pressure. The residue was diluted with water, filtered, dried and recrystallized from ethyl acetate:hexane to give crystals, m.p. 94°–97° C.

EXAMPLE 2

Preparation of 1-[p-(difluoromethylsulfinyl)phenyl]-1H-tetrazole

1-[p-(Difluoromethylthio)phenyl]-1H-tetrazole (1.0 gram) was added to a cold mixture of 5 ml. of concentrated sulfuric acid and 5 ml. of concentrated nitric acid and stirred for 40 minutes in the cold, then for 40 minutes at room temperature. The reaction mixture was poured onto ice and extracted with ethyl acetate. The ethyl acetate solution was extracted with water, dried over magnesium sulfate, and evaporated to afford an oil which was crystallized from ethyl acetate-hexane. Two recrystallizations from the same solvents gave 143 mg. of product, m.p. 109°–112° C.

EXAMPLE 3

Preparation of 1-[p-difluoromethylsulfonyl)phenyl]-1H-tetrazole

A mixture of 1-[p-(difluoromethylthio)phenyl]-1H-tetrazole (2.0 g.), 10 ml. of 30% of hydrogen peroxide, and 40 ml. of acetic acid was heated on a steambath for 4 hours, then diluted with 250 ml. of water. The crystalline product was collected, dried, and recrystallized from ethyl acetate:hexane to give the product, m.p. 162°–164° C.

EXAMPLE 4

Preparation of 1-[p-(fluoromethylthio)phenyl]-1H-tetrazole

In accordance with the procedure described in Example 1, treatment of p-(fluoromethylthio)aniline with triethylorthoformate and sodium azide furnishes the 1-[p-(fluoromethylthio)phenyl]-1H-tetrazole.

EXAMPLE 5

Preparation of 1-[p-(fluoromethylsulfinyl)phenyl]-1H-tetrazole

Treatment of 1-[p-(fluoromethylthio)phenyl]-1H-tetrazole with sulfuric acid and nitric acid by the procedure described in Example 2 is productive of the 1-[p-(fluoromethylsulfinyl)phenyl]-1H-tetrazole.

EXAMPLE 6

Preparation of 1-[p-(fluoromethylsulfonyl)phenyl]-1H-tetrazole

A mixture of p-(fluoromethylsulfonyl)aniline (0.85 g.), sodium azide (1.5 g.), triethyl orthoformate (10 ml.), and acetic acid (10 ml.) was heated at 85° C. for 5 hours and then evaporated at reduced pressure. The resulting residue was slurried in water and the insoluble solid filtered, dried, and recrystallized from ethyl acetate to give the product m.p. 171°–173° C. dec.

We claim:

1. A compound of the formula:

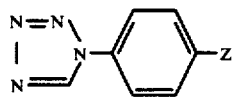

wherein Z is selected from the group consisting of fluoromethylthio, difluoromethylthio, fluoromethylsulfinyl, difluoromethylsulfinyl, fluoromethylsulfonyl and difluoromethylsulfonyl.

2. The compound according to claim 1 wherein Z is fluoromethylthio.

3. The compound according to claim 1 wherein Z is difluoromethylthio.

4. The compound according to claim 1 wherein Z is fluoromethylsulfinyl.

5. The compound according to claim 1 wherein Z is difluoromethylsulfinyl.

6. The compound according to claim 1 wherein Z is fluoromethylsulfonyl.

7. The compound according to claim 1 wherein Z is difluoromethylsulfonyl.

* * * * *